United States Patent
Moon (10) Patent No.: US 11,123,442 B2
(45) Date of Patent: Sep. 21, 2021

(54) GUANYLUREA FUNCTIONALIZED PEPTIDES AND PROTEINS FOR THERAPEUTICS

(71) Applicant: Joong Ho Moon, Weston, FL (US)

(72) Inventor: Joong Ho Moon, Weston, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/086,970

(22) Filed: Nov. 2, 2020

(65) Prior Publication Data

US 2021/0128747 A1     May 6, 2021

Related U.S. Application Data

(60) Provisional application No. 62/929,267, filed on Nov. 1, 2019, provisional application No. 62/987,075, filed on Mar. 9, 2020.

(51) Int. Cl.

| | |
|---|---|
| *A61K 47/69* | (2017.01) |
| *A61K 47/65* | (2017.01) |
| *B82Y 5/00* | (2011.01) |
| *A61K 31/282* | (2006.01) |
| *A61K 31/4745* | (2006.01) |
| *A61K 38/13* | (2006.01) |
| *A61K 31/337* | (2006.01) |

(52) U.S. Cl.
CPC ........ *A61K 47/6929* (2017.08); *A61K 31/282* (2013.01); *A61K 31/337* (2013.01); *A61K 31/4745* (2013.01); *A61K 38/13* (2013.01); *A61K 47/65* (2017.08); *B82Y 5/00* (2013.01)

(58) Field of Classification Search
CPC .................................................. A61K 47/6929
See application file for complete search history.

(56) References Cited

U.S. PATENT DOCUMENTS

| | | | |
|---|---|---|---|
| 10,017,462 B1* | 7/2018 | Moon | .................. C07D 241/04 |
| 10,568,902 B2* | 2/2020 | Moon | ..................... A61P 35/00 |
| 10,688,189 B1* | 6/2020 | Moon | .................. A61K 9/5146 |
| 2010/0255499 A1* | 10/2010 | Wender | .............. A61K 49/0013 |
| | | | 435/7.2 |

(Continued)

OTHER PUBLICATIONS

Elena A. Dubikovskaya, Steve H Thorne, Thomas H Pillow, Christopher H Contag, and Paul A. Wender. "Overcoming multidrug resistance of small-molecule therapeutics through conjugation with releasable octaarginine transporters." Proceedings of the National Academy of Sciences, 5(34), 2008, 12128-12133 (Year: 2008).*

(Continued)

*Primary Examiner* — Isaac Shomer
(74) *Attorney, Agent, or Firm* — Saliwanchik, Lloyd & Eisenschenk (57) ABSTRACT

A cell-penetrating peptide (CPP) comprising comprises a plurality of mono(amino acid)s, oligo(amino acid)s, or poly(amino acid)s where a plurality of the amino acids comprise a positively charged guanylurea unit with a small molecule fragment and each of the mono(amino acid)s, oligo(amino acid)s, or poly(amino acid)s comprising a drug attached through a linker. The CPP can be used for treating cancers.

16 Claims, 6 Drawing Sheets

(56) References Cited

U.S. PATENT DOCUMENTS

2011/0160146 A1* 6/2011 Wender ............... A61K 47/645
514/19.3
2019/0183923 A1* 6/2019 Moon ..................... A61P 35/00

OTHER PUBLICATIONS

Veerle Kersemans and Bart Cornelissen. Targeting the Tumour: Cell Penetrating Peptides for Molecular Imaging and Radiotherapy Pharmaceuticals 2010, vol. 3, ISSN 1424-8247, pp. 600-620. (Year: 2010).*

Rowena M. Briones, Ajit K. Sarmah. "Detailed sorption characteristics of the anti-diabetic drug metformin and its transformation product guanylurea in agricultural soils." Science of the Total Environment 630 (2018) 1258-1268. (Year: 2018).*

Karen Steward. "Amino Acids—the Building Blocks of Proteins." https://www.technologynetworks.com/applied-sciences/articles/essential-amino-acids-chart-abbreviations-and-structure-324357 accessed Jan. 21, 2021, originally published Sep. 26, 2019, pp. 1-18. (Year: 2019).*

Jessica R. Vargas, Erika Geihe Stanzl, Nelson N. H. Teng, and Paul A. Wender. "Cell-Penetrating, Guanidinium-Rich Molecular Transporters for Overcoming Efflux-Mediated Multidrug Resistance." Molecular Pharmaceutics, vol. 11, 2014, pp. 2553-2565. (Year: 2014).*

Jessica Renae Vargas. "The Development of New Methods for the Intracellular Delivery and Release of Messenger RNA and Other Biological Polyanions Using Amphipathic Molecular Transporters." Stanford University, PhD Thesis, Oct. 2016, p. i-xxxiv and 1-238. (Year: 2016).*

Md. Salauddin Ahmed et al. A guanylurea-functionalized conjugated polymer enables RNA interference in ex vivo human airway epithelium. Chemical Communications, vol. 55, 2019, pp. 7804-7807, published Jun. 12, 2019. (Year: 2019).*

Beck, A., et al., "Strategies and Challenges for the Next Generation of Antibody-Drug Conjugates." Nature Reviews Drug Discovery, May 2017, 16: 315-337.

Hatai, J., et al., "Diverse Properties of Guanidiniocarbonyl Pyrrole-Based Molecules: Artificial Analogues of Arginine." Accounts of Chemical Research, 2019, 52: 1709-1720.

Herce, H. D., et al., "Fundamental Molecular Mechanism for the Cellular Uptake of Guanidinium-Rich Molecules." Journal of the American Chemical Society, 2014, 136: 17459-17467.

Sugahara, K. N., et al., "Coadministration of a Tumor-Penetrating Peptide Enhances the Efficacy of Cancer Drugs." Science, May 2010, 328: 1031-1035.

Tsuchikama, K. et al., "Antibody-Drug Conjugates: Recent Advances in Conjugation and Linker Chemistries." Protein & Cell, 2018, 9(1): 33-46.

Vargas, J. R., et al., "Cell-Penetrating, Guanidinium-Rich Molecular Transporters for Overcoming Efflux-Mediated Multidrug Resistance." Molecular Pharmaceutics, 2014, 11: 2553-2565.

Zolot, R. S., et al., "Antibody-Drug Conjugates." Nature Reviews Drug Discovery, Apr. 2013, 12(4): 259-260.

* cited by examiner

Peptide (or protein or antibody)— —linker—-drug therapeutic peptides or proteins

-Increased bioavailability, shelf-life, blod circulation time

R=synthetic small molecules (e.g., various sizes of alchols, alkyl, alkenyl, alkynyl, phenyl, ethylene glycols etc), natural sugars (mono-, di-,-tri-, or polysaccharides), synthetic cross-linkers (mono, bi, tri, or hetero etc.)

C-terminal functiona groups

Carboxy, Hydrazid, Amide, Sulfonamide, Thiol, Ester, Alcohol, Thioacid, Lactam, Lactone, or Thioester Any types of cross-linkers (e.g., homo-, hetero, bi- or trifunctional) can be added to both C- and N-terminals.

Drug and Antibody can be added directly or indirectly (using any types of cross-linkers) to C- or N-terminals or both.

GU Class I
  $R_1$=H
  $R_2$= any lengths of hydrocarbons, hydrocarbons containing heteroatom(s), aromatic hydrocarbons, aromatic hydrocarbons containing heteroatom(s), or combinations of the above Class II      Class III
 $R_1$=$R_2$     $R_1$≠$R_2$

Class IV Drug or Antibody conjugated

R contains reactive functional group(s) such as isocyanate (reactive to alchols, amines, and thiols from drugs or antibodies), cross-linkers (homo-, hetero-, multifunctional groups will be used to couple drugs or antibodies), or any alcohols, amines, thiols, carboxylic acids, hydrizines, ketones, aldehydes, oximes, esters, amides, etc.)

FIG. 7

Dox-Y-R8(GU-PD)-SMPB
(Y = hydrazide)

Dox-Y-R8-SMPB

FIG. 8

GUANYLUREA FUNCTIONALIZED PEPTIDES AND PROTEINS FOR THERAPEUTICS

CROSS-REFERENCE TO RELATED APPLICATION

This application claims the benefit of U.S. Provisional Application Ser. No. 62/929,267, filed Nov. 1, 2019, and U.S. Provisional Application Ser. No. 62/987,075, filed Mar. 9, 2020, which are hereby incorporated by reference herein in their entirety, including any figures, tables, and drawings.

BACKGROUND OF INVENTION

Typical chemotherapies suffer from side effects associated with, for example, toxicity to normal cells and drug resistance. Antibody-drug conjugates (ADCs) have been used to treat various diseases owing to improved targeting ability. Because of the targeting specificity of monoclonal antibodies (mAbs), highly toxic anticancer drugs can be selectively delivered to a target site. To further increase the targeting efficacy of ADCs, modifications are introduced to increase the bioavailability of ADCs, improve the blood circulation time, and enhance the drug release. Currently, clinically used ADCs display low overall therapeutic efficacy for one or more of these reasons. In spite of the progress made in advanced protein engineering and bioconjugation techniques, current ADCs display poor and slow cellular entry leading to unsatisfactory therapeutic concentrations delivered to the target cells. For example, mAbs have sizes that preclude diffusion through a tumor's interstitial space and endocytosis of ADCs is typically slow and inefficient. Also, linkers sensitive to a tumor's extracellular environment can release small drugs at the target tissue, but small drugs are substrates for various efflux pumps that are overexpressed in most cancer cells, which lowers intracellular drug concentrations and results in drug resistance.

Coupling a drug to large molecules that are not substrates of efflux pumps and exhibit excellent intracellular entry, such as cell-penetrating peptides, could address this problem. However, most cell-penetrating molecules are positively charged lipophilic compounds that have limited diffusion through a tumor's extracellular environment. Therefore, a drug conjugate that is not a substrate of efflux pumps and offers high intracellular availability through efficient diffusion through the tumor extracellular matrix (ECM) for fast transmembrane entry is desirable to improve ADC-based therapeutics.

Nanocarriers for drugs tend to accumulate in relatively loosely organized tumor tissue as opposed to tight normal tissue if the carriers can remain in blood circulation for a sufficient period. Inefficient diffusion of nanocarriers through a tumor's interstitial space limits the availability of therapeutics deep inside the tumor, which contributes to drug resistance and poor therapeutic outcome. Nanocarriers are too big to effectively diffuse through the charged extracellular environment.

Poly(ethylene glycol)s (PEGs) and zwitterion modifications to nanocarriers have increased blood circulation times for nanocarriers. These modifications result in hydrophilic and steric layers that reduce or avoid recognition and clearance by the immune system, but their poor cellular entry is limiting. Synthetic PEGs have led to an increase in immunogenicity of PEGylated nanomedicines. Polydispersity-related issues have been observed for synthetic PEGs or zwitterion containing polymers, which limit the precise tuning of in vivo properties. Therefore, an innovative technique to enhance cellular entry efficiency while maintaining long circulation is needed.

Stimuli responsive nanocarriers that release drugs at the tumor tissues have shown promise at improving therapeutic efficacy. However, drug resistance due to the presence of the efflux pumps overexpressed in many tumor cells remains a concern. Wender et al. demonstrated that a Taxol-coupled oligoarginine peptide exhibits promising results in malignant human ascites. Coupling the drug to cell-penetrating oligoarginine allows efficient cellular entry of the drug-peptide conjugate, which is not a substrate for an efflux pumps. Despite the promising outcomes, the unshielded positive charges of drug-conjugates remains an issue for clinical translation. Complexation or coupling to negatively charged glycosaminoglycans, hyaluronic acid or chondroitin sulfate, addresses in vivo circulation issues of positively charged complexes. However, poor and inefficient intracellular entry of these nanomedicines remains a major issue that lowers the overall therapeutic efficacy.

Hydrophilic bulky PEG and zwitterions lack a necessary interaction between the drug carriers with the negatively charged hydrophobic cell membranes. Hence, positive charges appear to be needed for effective cellular entry, even those with positive charges have been related to various toxicity and poor in vivo behaviors. Traditional endocytosis-mediated entry is often slow and inefficient, as these endocytosed therapeutic agents often face harsh degradation or recycling processes that lower the intracellular concentration of therapeutic agents.

Thus, there is a need for modulation that is applicable to existing carriers and therapeutics without requiring complicated chemical formulation processes. There is also a need to introduce well-defined small molecule to positive charges of carriers at near ambient temperatures by mild modulation chemistry that can be applicable to small drugs, peptides, proteins, lipids, micelles, or synthetic/natural polymers to enhance tumor targeting and cellular entry of therapeutics.

BRIEF SUMMARY

The subject invention provides materials and methods for intracellularly delivering small molecules such as drugs, nucleic acids, and peptides, as well as proteins and other larger molecules. The subject invention also provides materials and methods for assisting the passage of molecules across biological membranes.

In one embodiment, the subject invention provides a linker peptide or linker protein comprising a plurality of oligo(amino acid)s or poly(amino acid)s, wherein a plurality of the amino acid residues comprise one or more positively charged guanylurea units, and optionally, one or more positively charged guanylurea units are modified, preferably, with one or more small molecule fragments.

In one embodiment, the linker peptide or linker protein according to the subject invention comprises one or more oligopeptides or polypeptides, wherein a plurality of the amino acid residues comprise one or more positively charged guanylurea units, and optionally, one or more positively charged guanylurea units are modified, preferably, with one or more small molecule fragments.

In one embodiment, the subject invention provides a peptide-active agent comprising a plurality of oligo(amino acid)s or poly(amino acid)s, wherein a plurality of the amino acid residues comprise one or more positively charged guanylurea units, and optionally, one or more positively charged guanylurea units are modified with one or more small molecule fragments, and wherein each of the oligo (amino acid)s or poly(amino acid)s comprises an active agent (e.g., a drug or a detectable entity) attached through a linker.

In one embodiment, the subject invention provides a peptide-active agent comprising the linker peptide or linker protein according to the subject invention, and an active agent. In specific embodiments, the peptide-active agent comprises one or more oligopeptides or polypeptides, wherein a plurality of the amino acid residues comprise one or more positively charged guanylurea units, and optionally, one or more positively charged guanylurea units are modified with one or more small molecule fragments, and wherein the oligopeptide or polypeptide comprises an active agent (e.g., a drug or a detectable entity) attached through a linker.

In one embodiment, the subject invention provides a cell-penetrating peptide (CPP) comprising nanoparticle (NP), comprising a plurality of oligo(amino acid)s or poly (amino acid)s, where a plurality of the amino acid residues comprise a positively charged guanylurea unit with a small molecule fragment/modification, and each of the oligo (amino acid)s or poly(amino acid)s comprises an active agent (e.g., a drug or a detectable entity) attached through a linker, and a plurality of crosslinks. The NP is stable in the bloodstream or in healthy cells but decomposes to the CPPs in the environment of the tumor cells to provide the drug to the tumor cell.

In one embodiment, the small molecule fragment comprises a polyol comprising 2 to 20 hydroxy groups, or propanediol, wherein the polyol comprises a sugar.

In one embodiment, the linker may be mono, bi, or trifunctional cross-linker comprising, for example, hydrazone, esters (e.g., NHS-ester), amides, azides, oxyme, meleimide, b-iodo or disulfide. In specific embodiments, the drug comprises a radio therapeutic, doxorubicin, paclitaxel, thapsigargin, cyclosporine A, or cis-platinum.

In one embodiment, the crosslinker comprises a bis-boronic acid residue, wherein the bis-boronic acid residue comprises a drug.

In one embodiment, the subject invention provides ADCs comprising a plurality of oligo(amino acid)s or poly(amino acid)s, wherein a plurality of the amino acid residues comprise one or more positively charged guanylurea units, and optionally, one or more positively charged guanylurea units are modified, preferably, with one or more small molecule fragments, and wherein each of the oligo(amino acid)s or poly(amino acid)s comprises an active agent (e.g., a drug or a detectable entity) attached through a linker and a targeting moiety (e.g., antibody) attached through a second linker/crosslinker.

In one embodiment, the subject invention provides an ADC comprising the linker peptide or linker protein according to the subject invention, an active agent, and a targeting moiety. In specific embodiments, the ADC comprises one or more oligopeptide or polypeptide, wherein a plurality of the amino acid residues comprise one or more positively charged guanylurea units with one or more small molecule fragments/modifications, and wherein the oligopeptide or polypeptide comprises an active agent (e.g., a drug or a detectable entity) attached through a linker and a targeting moiety (e.g., antibody) attached through a second linker/crosslinker.

In one embodiment, the subject invention provides a method of preparing the linker peptide or linker protein of the subject invention. The method comprises providing a tritylated peptide, poly(amino acid)s or protein comprising one or more guanidine units; and linking one or more guanidine units to one or more small molecules/small molecule fragments/functional groups to form guanylurea units with the small molecules/small molecule fragments/modifications.

In one embodiment, the subject invention provides a method of preparing a peptide-active agent of the subject invention. The method comprises providing a tritylated peptide, poly(amino acid)s or protein comprising a guanylurea linked to a small molecule/small molecule fragment/modification; and coupling the tritylated peptide, poly (amino acid)s or protein to a drug through a linker to form a peptide-active agent.

In one embodiment, the subject invention provides a method of preparing a CPP-NP of the subject invention, comprising:

providing a tritylated protein, peptide or fragment thereof comprising a guanylurea linked to a small molecule;

coupling the tritylated protein, peptide or fragment thereof to a drug through a linker to provide a drug comprising peptide; and combining the drug comprising peptide with a crosslinker to form a CPP-NP. wherein the crosslinker is a bis-boronic acid.

In one embodiment, the subject invention provides a method of treatment of a tumor, comprising administering to the tumor a CPP-NP of the subject invention.

In one embodiment, the subject invention also provides methods for treating a cancer, the method comprising administering, to a subject in need of such treatment, an effective amount of the peptide-active agent/CPP/ADC of the subject invention.

In one embodiment, the subject invention further provides methods for delivering a therapeutic agent into a cancer cell, the method comprising contacting the cancer cell with the peptide-active agent/CPP/ADC of the subject invention.

DETAILED DISCLOSURE

The subject invention provides materials and methods for intracellularly delivering small molecules such as drugs, nucleic acids, peptides, antibodies, and sensors (e.g., dyes) as well as proteins and other larger molecules. The subject invention also provides materials and methods for assisting the passage of molecules across biological membranes.

In one embodiment, the subject invention provides nanomaterials as molecule transporters for targeted delivery of therapeutic agents into cells, preferably, cancer cells for inhibiting the growth of cancer cells.

In one embodiment, the subject invention provides novel and advantageous linker molecules for coupling, for example, an antibody to one or more molecules. The subject invention also provides a peptide-active agent, antibody-drug conjugates (ADCs), cell-penetrating peptides (CPPs), CPP-nanoparticles (CPP-NP), and applications thereof.

In one embodiment, the linker molecule according to the subject invention comprises a plurality of oligo(amino acid)s or poly(amino acid)s, wherein a plurality of the amino acid residues comprise one or more positively charged guanylurea units. The oligo(amino acid)s or poly(amino acid)s may be a peptide/protein/antibody that is functional or nonfunctional, therapeutic or non-therapeutic, and/or guanidine-containing or non-guanidine-containing. The amino acid may be natural or non-natural, or modified or non-modified amino acids.

In one embodiment, the oligo(amino acid)s or poly(amino acid)s can be peptides with any length. The numbers of amino acid in the oligo(amino acid)s or poly(amino acid)s may be, for example, at least 2, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100. The oligo(amino acid)s or poly(amino acid)s may be linear, cyclic or acyclic.

In one embodiment, the linker molecule of the subject invention is a linker peptide or linker protein. The linker peptide or linker protein of the subject invention comprises a plurality of oligo(amino acid)s or poly(amino acid)s, wherein a plurality of the amino acid residues comprise one or more positively charged guanylurea units with one or more small molecule fragments/modifications.

In one embodiment, the linker peptide or linker protein according to the subject invention comprises an oligopeptide or polypeptide, wherein a plurality of the amino acid residues of the oligopeptide or polypeptide comprise one or more positively charged guanylurea units with one or more small molecule fragments/modifications. In specific embodiments, the modification may be hydrophobic or hydrophilic modifications.

In one embodiment, the oligopeptide, polypeptide, oligo(amino acid)s or poly(amino acid)s comprise one or more arginine residues. The numbers of arginine in the oligo(amino acid)s or poly(amino acid)s may range, for example, from about 1 to about 500, from about 1 to about 400, from about 1 to about 300, from about 1 to about 200, from about 1 to about 100, from about 2 to about 500, from about 2 to about 400, from about 2 to about 300, from about 2 to about 200, from about 2 to about 100, from about 2 to about 90, from about 2 to about 80, from about 2 to about 70, from about 2 to about 60, from about 2 to about 50, from about 2 to about 40, from about 2 to about 30, from about 2 to about 20, from about 2 to about 10, from about 1 to about 90, from about 1 to about 80, from about 1 to about 70, from about 1 to about 60, from about 1 to about 50, from about 1 to about 40, from about 1 to about 30, from about 1 to about 20, from about 1 to about 10, from about 5 to about 90, from about 5 to about 50, from about 5 to about 30, from about 10 to about 50, or from about 10 to about 30.

In one embodiment, the oligopeptide, polypeptide, oligo(amino acid)s or poly(amino acid)s may have a structure of $(Arg)x(any\ amino\ acid)y$, wherein each x, and $y \geq 1$, preferably, $2 \leq x+y \leq 200$, $2 \leq x+y \leq 150$; $2 \leq x+y \leq 120$, $2 \leq x+y \leq 90$; $2 \leq x+y \leq 80$, $2 \leq x+y \leq 70$, $2 \leq x+y \leq 60$, $2 \leq x+y \leq 50$, $2 \leq x+y \leq 40$, or $2 \leq x+y \leq 30$.

In one embodiment, the oligopeptide, polypeptide, oligo(amino acid)s or poly(amino acid)s may have a structure of $(any\ amino\ acid)z(Arg)x(any\ amino\ acid)y$, wherein each x, y, and $z \geq 1$, preferably, $3 \leq x+y+z \leq 200$, $3 \leq x+y+z \leq 150$; $3 \leq x+y+z \leq 120$, $3 \leq x+y+z \leq 90$; $3 \leq x+y+z \leq 80$, $3 \leq x+y+z \leq 70$, $3 \leq x+y+z \leq 60$, $3 \leq x+y+z \leq 50$, $3 \leq x+y+z \leq 40$, or $3 \leq x+y+z \leq 30$.

In some embodiments, the oligopeptide, polypeptide, oligo(amino acid)s or poly(amino acid)s comprise one or more arginine residues and any other amino acids distributed randomly (e.g., -Arg-Xaa-Arg-Xaa-Xaa-Xaa-), or arranged in an alternating sequence (e.g., -Arg-Xaa-Arg-Xaa-Arg-Xaa-), periodic repeating sequence (e.g., -(Arg-Xaa-Arg-Xaa-Xaa-Xaa)m-) or block sequence (e.g., -Arg-Arg-Arg-Xaa-Xaa-Xaa-).

In one embodiment, the oligopeptide, polypeptide, oligo(amino acid)s or poly(amino acid)s are homo peptides comprising a plurality of arginine residues, i.e., $(Arg)n$, wherein $n \geq 2$. Preferably, $2 \leq n \leq 200$, $2 \leq n \leq 150$; $2 \leq n \leq 120$, $2 \leq n \leq 90$; $2 \leq n \leq 80$, $2 \leq n \leq 70$, $2 \leq n \leq 60$, $2 \leq n \leq 50$, $2 \leq n \leq 40$, or $2 \leq n \leq 30$.

In one embodiment, the oligopeptide, polypeptide, oligo(amino acid)s or poly(amino acid)s comprise a plurality of the amino acid residues comprising one or more positively charged guanylurea units or modified guanylurea units. Such guanylurea unit or modified guanylurea unit comprises the group of wherein $R_1$ and $R_2$ are independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, amino, alkylamino, arylamino, and hydroxylalkyl.

In one embodiment, $R_1$ and $R_2$ independently comprise any lengths of hydrocarbons, hydrocarbons containing heteroatom(s), aromatic hydrocarbons, aromatic hydrocarbons containing heteroatom(s), or any combinations thereof.

In one embodiment, $R_1$ and $R_2$ are independently selected from, for example, N-alkylamino; N-arylamino; N-(alkylaryl)amino; N-(aryalkyl)amino; N, N-dialkylamin; N, N-diarylamino; N, N-di(alkylaryl)amino; N, N-di(aryalkylamino); N-alkyl, N-arylamino; N-alkyl, N-(alkylaryl)amino; N-alkyl, N-(arylalkyl)amino; N-aryl, N-(alkylaryl)

amino; N-aryl, N-(arylalkyl)amino; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; unsubstituted or substituted carbazole; imidazole or substituted imidazole; purine or substituted purine; aminoethanol; amino terminal polyethylene oxide, substituted or unsubstituted alky carbamate, substituted or unsubstituted aryl carbamate, substituted or unsubstituted alkylaryl carbamate, substituted or unsubstituted aryalkyl carbamante, substituted or unsubstituted phenyl, ethylene glycols, natural sugars (mono-, di-, tri- and polysaccharides) and synthetic cross-linkers (e.g., mono, bi, tri, and hetero multifunctonal groups).

In a preferred embodiment, $R_1$ and $R_2$ are independently selected from, for example, hydrogen, alkyl, alkenyl, alkynyl, phenyl, alcohol, and alkylhalides. In a specific embodiment, $R_1$ and $R_2$ are independently selected from, for example, hydrogen,

$m \geq 1$.

In a specific embodiment, the linker peptide of the subject invention comprises a structure of wherein $R_1$ and $R_2$ can be the same or different.

In one embodiment, the guanylurea unit or modified guanylurea unit may comprise the functional group of wherein $L_2$ is a linker and can be null; R is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, amino, alkylamino, arylamino, and hydroxylalkyl.

In one embodiment, R comprises any lengths of hydrocarbons, hydrocarbons containing heteroatom(s), aromatic hydrocarbons, aromatic hydrocarbons containing heteroatom(s), or any combinations thereof.

In one embodiment, R is selected from, for example, N-alkylamino; N-arylamino; N-(alkylaryl)amino; N-(aryalkyl)amino; N, N-dialkylamin; N, N-diarylamino; N, N-di(alkylaryl)amino; N, N-di(aryalkylamino); N-alkyl, N-arylamino; N-alkyl, N-(alkylaryl)amino; N-alkyl, N-(arylalkyl)amino; N-aryl, N-(alkylaryl)amino; N-aryl, N-(arylalkyl)amino; unsubstituted or substituted morpholine; unsubstituted or substituted pyrolidine; unsubstituted or substituted pyrrole; unsubstituted or substituted piperidine; unsubstituted or substituted ethyleneimine; unsubstituted or substituted indole; unsubstituted or substituted isoindole; unsubstituted or substituted carbazole; imidazole or substituted imidazole; purine or substituted purine; aminoethanol; amino terminal polyethylene oxide, substituted or unsubstituted alky carbamate, substituted or unsubstituted aryl carbamate, substituted or unsubstituted alkylaryl carbamate, substituted or unsubstituted aryalkyl carbamante, substituted or unsubstituted phenyl, ethylene glycols, natural sugars (mono-, di-, tri- and polysaccharides) and synthetic cross-linkers (e.g., mono, bi, tri, and hetero multifunctonal groups).

In one embodiment, R may contain reactive functional group(s) such as isocyanate (reactive to alchols, amines, and thiols from drugs or antibodies), any alcohols, amines, thiols, carboxylic acids, hydrizines, ketones, aldehydes, oximes, esters, or amides.

In some embodiments, $L_2$ may be selected from alkyl, alkenyl, alkynyl, aromatics, heteroalkyl, heteroaryl, cycloalkyl, and heterocyclyl. Preferably, $L_2$ is selected from C1-C10 alkyls, C2-C10 alkenyls, C2-C10 alkynyls, C3-C10 cycloalkyls, and C3-C10 heterocyclyls.

In one embodiment, the subject invention provides a peptide-active agent comprising the linker molecule of the subject invention. The peptide-active agent of the subject invention comprises a plurality of oligo(amino acid)s or poly(amino acid)s, wherein a plurality of the amino acid residues comprise one or more positively charged guanylurea units with one or more small molecule fragments/modifications, and each of the oligo(amino acid)s or poly(amino acid)s comprises an active agent (e.g., a drug or a detectable entity) attached through a linker. In one embodiment, the subject invention provides a peptide-active agent comprising an oligopeptide or polypeptide, wherein the oligopeptide or polypeptide comprises one or more positively charged guanylurea units with one or more small molecule fragments/modifications, and wherein the oligopeptide or polypeptide further comprises an active agent (e.g., a drug or a detectable entity) attached through a linker.

In one embodiment, the small molecule fragment comprises a polyol comprising 2 to 20 hydroxy groups, or propanediol, wherein the polyol comprises a sugar.

In one embodiment, the linker may comprise, or be, mono, bi, or trifunctional cross-linkers comprising, for example, hydrazide, hydrazone, esters (e.g., NHS-ester), amides, azides, oxyme, meleimide, b-iodo, disulfide or any peptides (e.g., enzyme specific degradable peptides).

In one embodiment, the drug may be any therapeutic agents, for example, a radio therapeutic, doxorubicin, paclitaxel, thapsigargin, cyclosporine A, or cis-platinum.

In one embodiment, the peptide-active agent of the subject invention may have a structure of $M-Y_m-D$, wherein M is the linker peptide or linker protein of the subjection invention; Y is a linker or can be null; $m \geq 0$; D is an active agent, for example, a drug or a detectable entity (e.g., a dye molecule). In one embodiment, the active agent can be attached to C-, N-, or both terminals of the linker peptide or linker protein. In some embodiments, the active agent may be attached to the backbone of the oligopeptide, polypeptide, oligo(amino acid)s or poly(amino acid)s, and/or the side chain(s) of the oligopeptide, polypeptide, oligo(amino acid)s or poly(amino acid)s.

In a preferred embodiment, Y is a reducible linker. In a specific embodiment, Y is a linker formed by reacting $p \geq 0$, e.g., with M, the linker peptide or linker protein of the subject invention. Advantageously, once delivered intracellularly, the Y linker can be reduced to release the active agent from the peptide-active agent.

In one embodiment, the peptide-active agent of the subject invention further comprises a crosslinker that can react with, for example, an antibody.

In one embodiment, the peptide-active agent of the subject invention may form nanoparticles comprising the active agent.

In one embodiment, the subject invention also provides ADCs comprising the linker molecule of the subject invention. The ADCs of the subject invention comprise a plurality of oligo(amino acid)s or poly(amino acid)s, wherein a plurality of the amino acid residues comprise one or more positively charged guanylurea units with one or more small molecule fragments/modifications, and each of the oligo(amino acid)s or poly(amino acid)s comprises an active agent (e.g., a drug or a detectable entity) attached through a linker and a targeting moiety (e.g., antibody) attached through a second linker/crosslinker.

In one embodiment, the ADC comprises an oligopeptide or polypeptide, wherein a plurality of the amino acid residues comprise one or more positively charged guanylurea units with one or more small molecule fragments/modifications, and wherein the oligopeptide or polypeptide comprises an active agent (e.g., a drug or a detectable entity) attached through a linker and a targeting moiety (e.g., antibody) attached through a second linker/crosslinker.

In one embodiment, the ADCs of the subject invention may have a structure of $A-(L_1)_o-M-Y_m-D$, wherein M is the linker peptide or linker protein of the subjection invention; Y is a linker or can be null; $L_1$ is a linker, crosslinker or can be null; each o and $m \geq 0$; D is an active agent, for example, a drug or a dye molecule; and A is a targeting moiety.

In one embodiment, the active agent and targeting moiety can be attached to C-, N- or both terminals of the linker peptide or linker protein. In some embodiments, the active agent and targeting moiety may be attached to the backbone of the oligopeptide, polypeptide, oligo(amino acid)s or poly(amino acid)s, and/or the side chain(s) of the oligopeptide, polypeptide, oligo(amino acid)s or poly(amino acid)s.

In a preferred embodiment, Y is a reducible linker. In a specific embodiment, Y is a linker formed, for example, by reacting $p \geq 0$, e.g., with M, the linker peptide or linker protein of the subject invention.

Advantageously, once the ADCs of the subject invention is brought to the target through the recognition by the targeting moiety, the Y linker can be reduced to release the active agent from the ADCs.

In a specific embodiment, $L_1$ may be, for example, m-maleimidobenzoyl-N-hydroxysuccinimide ester (MBS), succinimidyl 4-(p-maleimidophenyl)butyrate (SMPB), disuccinimidyl tartrate (DST), disuccinimidyl suberate (DSS), disuccinimidyl glutarate (DSG), bis(sulfosuccinimidyl)suberate (BS3), dimethyl suberimidate (DMS), N-α-maleimidoacet-oxysuccinimide ester (AMAS), or N-β-maleimidopropionic acid hydrazide (BMPH). In a specific embodiment, the crosslinker comprises a bis-boronic acid.

In some embodiments, $L_1$ may be a linker or crosslinker comprising a functional group. Such functional group may comprise a maleimide, halogen, halogen-substituted functional group, alkanal, alkanone, sulfonyl-alkene, silane, isocyanate, or norbornene. The functional group may be able to react with a thiol. In certain embodiments, $L_1$ may comprise $C_1-C_6$ alkyls, $C_2-C_6$ alkenyls, $C_2-C_6$ alkynyls, aromatics, heteroaryls, $C_3-C_9$ cycloalkyls, $C_3-C_9$ heterocyclyl, polyethylene glycol, O, S, C(=O), C(=O)O, C(=S)O, S(=O)$_2$ or any combination thereof.

In some embodiments, A is an antibody; an antibody fragment, surrogate or variant; a protein ligand; a protein scaffold; a peptide; or a small molecule ligand. The antibody fragment can be, for example, Fab, Fab', (Fab')2, or scFv, Fv. The target moiety selectively binds to the analyte/target of interest. In a specific embodiment, the analyte is HER2, or other antigen associated with cancers, including, for example, CD44, CD24, CD133, EpCAM, ABCG2, ABCB1, EGFR, TUBB4B, CDK 2, CDK4, CDK6, CDK12, MET, MCL, AKT1, ESR1, TYMS, PIK3CB, PIK3CA, IGF1R, MTOR, ALDH, and ATR.

In some embodiments, the linker peptide or linker protein of the subject invention may be attached to a detectable entity as the active agent. In other embodiments, the peptide-active agent and/or ADC of the subject invention comprise a detectable entity as the active agent. The detectable entity may be, for example, a visualization agent. The agent can be a synthetic or natural product, and capable of reflecting or emitting light at a wavelength detectable by suitable imaging and/or diagnostic equipment such as a microscope. Non-limiting examples of suitable visualization agents include organic dyes, food dyes, and fluorescence dyes.

In one embodiment, the visualization agent may be, for example, fluorescein, TAMRA, rhodamine, Texas Red, Alexa Fluor (e.g., AlexaFluor 488, AlexaFluor 532, AlexaFluor 546, AlexaFluor 594, AlexaFluor 633 and AlexaFluor 647), cyanine dye (e.g., Cy7, Cy7.5, Cy5, Cy5.5 and Cy3), Tye dye (e.g., TYE 563, TYE 665, TYE 705), atto dye (e.g., Atto 594 and Atto 633), Hexachlorofluorescein, FAM (6-carboxyfluroescein), BODIPY FL, OliGreen, 40,6-diamidino-2-phenylindol (DAPI), Hoechst 33,258, malachite green (MG), IR780 and FITC.

Advantageously, the peptide-active agents/CPPs and/or ADCs of the subject invention comprise guanylurea units and/or modified guanylurea units that are useful for enhanced intracellular drug delivery, specific targeting and pharmacokinetics. Novel chemistry and engineering of the positive charges provide balanced ionic interaction that prevents nonspecific interaction from the serum proteins but offers efficient diffusion through the extracellular environments and entry through the membranes.

The reaction between the guanidine and functional groups (e.g., amines, PEG and isocyanate) at room temperature results in guanylurea formation. This mild and bio-friendly condition can introduce nonionic hydrophilic molecules at the positive charge via the urea extension. The guanylurea chemistry is simple but highly efficient for introducing naturally available or molecularly defined synthetic functional groups at the positive charge of carriers.

Figure 1:
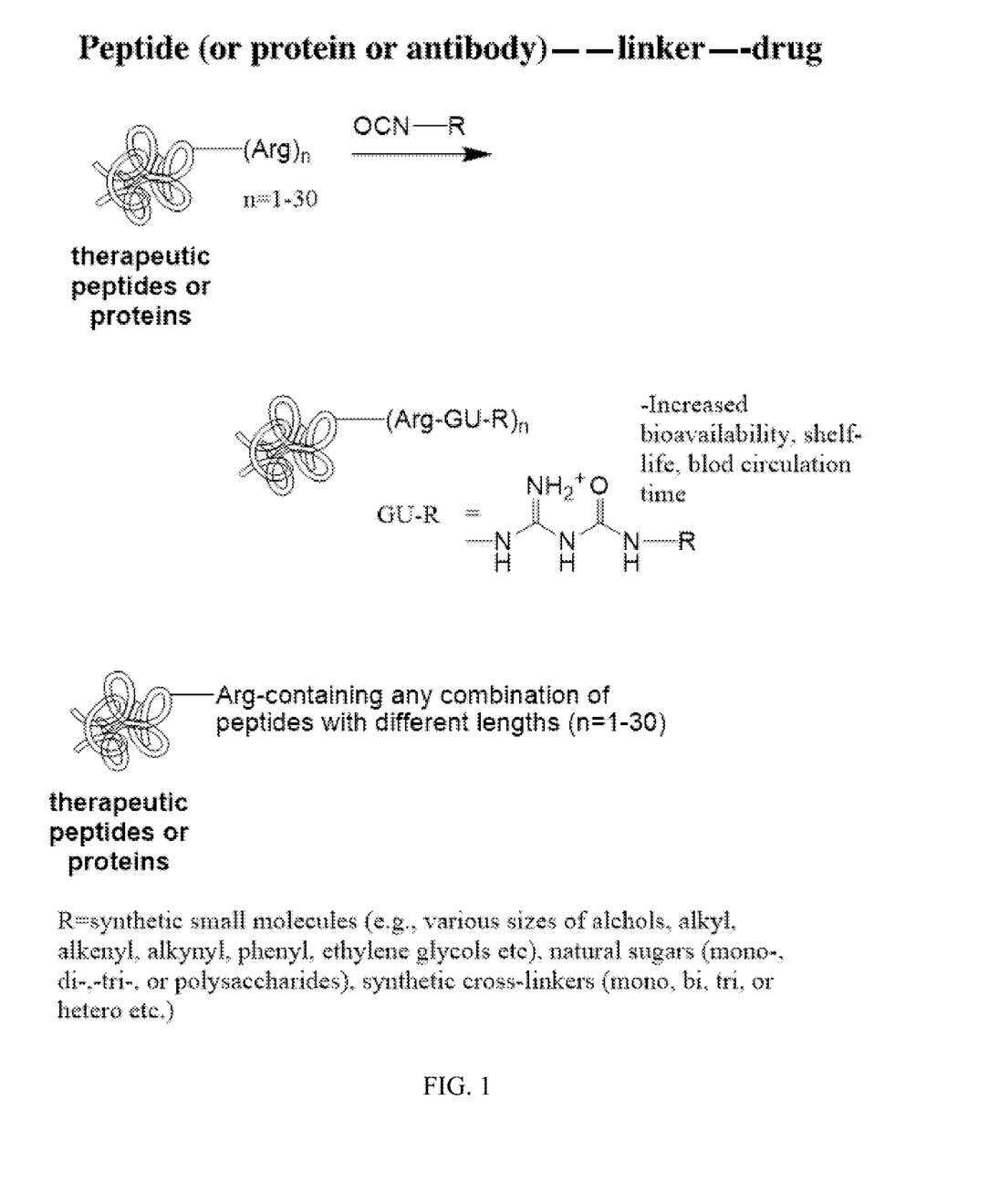
FIG. 1 gives a synopsis of the cell-penetrating peptide (CPP) formation and scope of the peptide, linker, drug, and small molecule attached via a guanylurea, according to an embodiment of the invention.

An embodiment of the invention is directed to nanoparticles (NPs) of a cell-penetrating peptide (CPP) where positive charges balance ionic interaction that prevents nonspecific interaction from the serum proteins but offers efficient diffusion through the extracellular environments and entry through cancer cell membranes. By an ambient temperature reaction between guanidine and an isocyanate group, a guanylurea forms to introduce nonionic hydrophilic molecules at a positive charge via the urea extension as shown in FIG. 1. The guanylurea functionalization enables efficient small interfering RNA complexation and mucus penetration. Highly efficient diffusion is observed by guanylurea-modulation, which is in contrast to purely positively charged polymers that show no diffusion through the mucus layer. The guanylurea functionalization allows cellular entry.

As the active functional group of cell-penetrating peptides (CPPs) and protein transduction domains, guanidine undergoes ionic and hydrogen-bonding (H-bonding) with the phospholipids of the cellular membrane. Bidentate H-bonding followed by insertion of hydrophobic units into the membrane appears to allow highly efficient membrane translocation of CPPs and/or ADCs.

Figure 2:
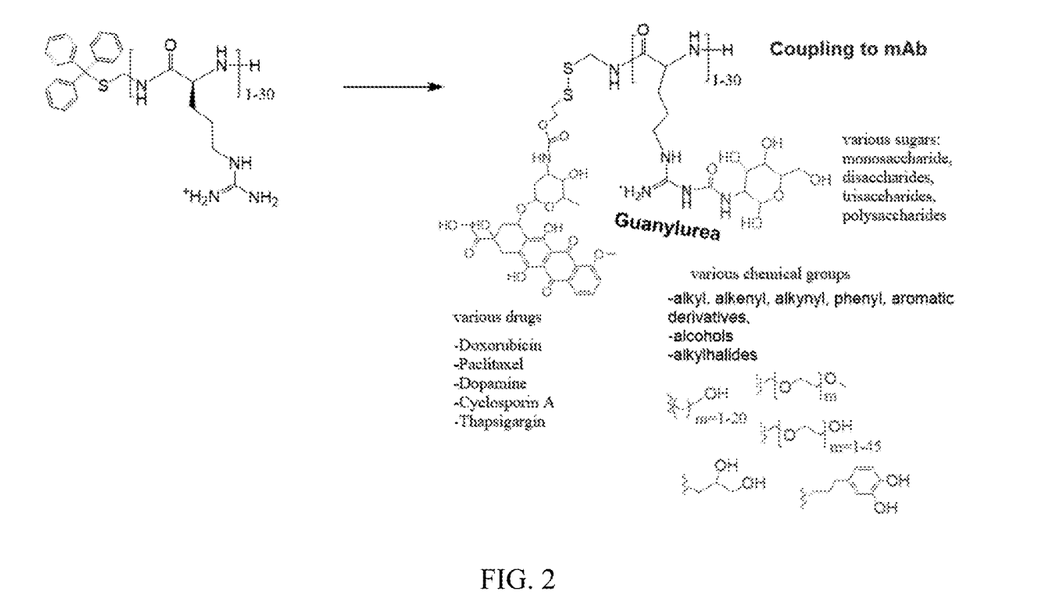
FIG. 2 shows a reaction scheme for the formation of a CPP by formation of a guanylurea attachment of a polyol at every guanidine amino acid repeating unit and an end-functionalized drug (Doxuribicin, Dox), according to an embodiment of the invention.
Figure 3:
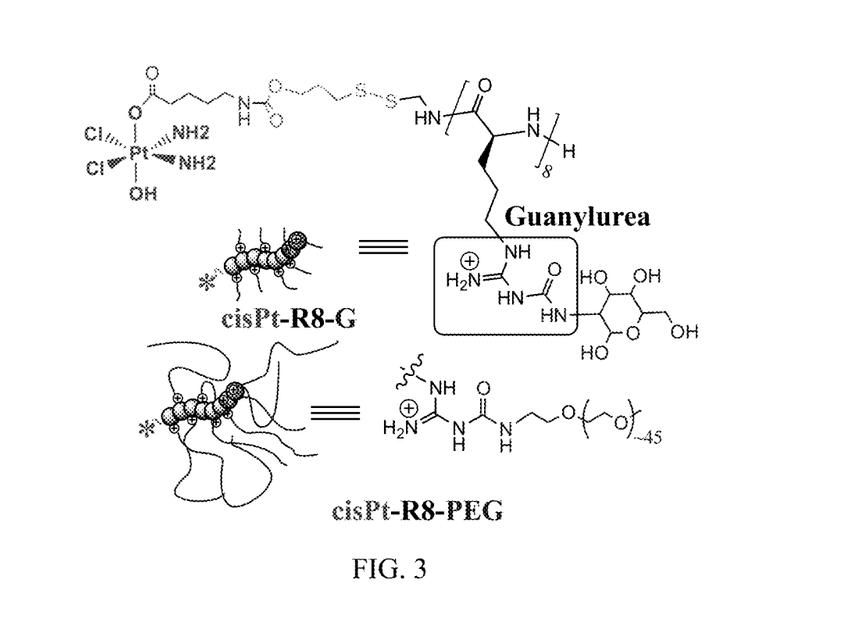
FIG. 3 shows an exemplary cis-Pt-octaarginine (R8)-guanylurea-sugar CPP according to an embodiment of the invention, and a contrasting cis-Pt-octaarginine (R8)-guanylurea-PEG.

The guanylurea allows increased H-bonding through an introduced urea bond and introduces alcohols, as shown by the monosaccharide in FIG. 2. The guanylurea chemistry is highly efficient for readily introducing natural or synthetic functional groups at a positive charge of carriers, in contrast to other polymeric approach, such as PEG or zwitterion polymers usage. Various carbohydrates, which are common component of blood, or PEG act as biological shielding groups for various nanomedicines or ADCs attached to the CPP, as shown in FIG. 3.

Figure 4:
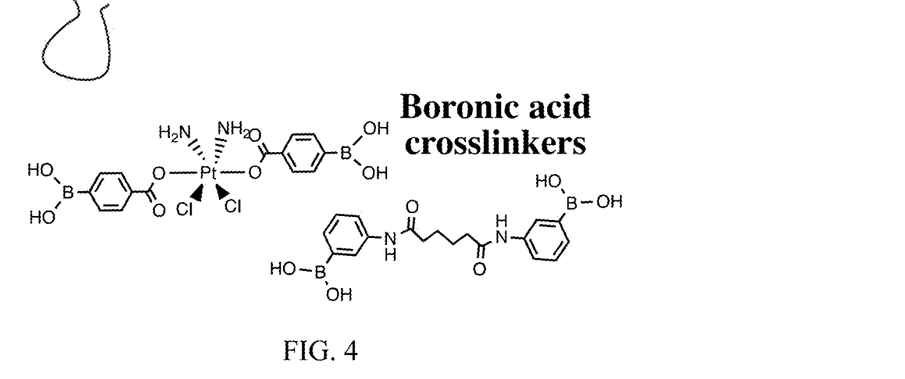
FIG. 4 shows bis-boronic acid crosslinkers according to an embodiment of the invention including and excluding a drug for crosslinking of the CPP, according to an embodiment of the invention, to form nanoparticles (NPs), according to an embodiment of the invention.

In an exemplary embodiment, a short octaarginine (R8) CPP is useful as the primary component of a drug carrier. Arginine-rich peptides have been used to deliver nucleic acids, proteins, and small drugs due to high cellular entry. However, the positively charged peptide alone, displays non-specific binding to non-targeted cells, poor bioavailability, opsonization, and recognition by circulating macrophages, limiting any clinical use. The modulated peptide is converted into a CPP-NP via a phenylboronic acid-sugar interaction. This reversible boronic ester formation acts as a crosslink for the exemplary drug-R8-G. The bis-boronic ester crosslinker, as shown in FIG. 4, can be a prodrug unit in addition to any drug otherwise conjugated to the peptide.

After accumulation at the tumor, NPs degrade to the drug-conjugated peptides by decomposition of the acid-labile boronic ester bond in the presences of sialic acids that are overexpressed in the tumor extracellular environments and have much stronger binding affinity to boronic acid. In a typical acidic tumor environment, for example, pH 6.5, the binding constant of phenylboronic acid with sialic acid is about an order of magnitude greater than that with other sugars. This labile crosslinking results in NP destabilization in the presence of the tumor cell, decreases non-specific release of drug in the blood or to normal tissue where the boronic ester bond is stable at neutral or basic pH. The NPs display a long blood circulation time due to a high density of hydrophilic sugar molecules at the positive charges, to promote high accumulation at the tumor.

In one embodiment, the subject invention provides a therapeutic formulation comprising the linker molecule of the subject invention and a pharmaceutically acceptable carrier, wherein the therapeutic formulation further comprises one or more active agents.

In one embodiment, the subject invention provides a composition comprising the peptide-active agent of the subject invention and a pharmaceutically acceptable carrier. The subject invention also provides a composition comprising the CPP of the subject invention and a pharmaceutically acceptable carrier. The subject invention further provides a composition comprising the ADC of the subject invention and a pharmaceutically acceptable carrier.

"Pharmaceutically acceptable carrier" refers to a diluent, adjuvant or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

In one embodiment, the subject invention provides a method of preparing the peptide linker or protein linker of the subject invention. The method comprises providing a tritylated peptide, poly(amino acid)s or protein comprising one or more guanidine units; and linking one or more guanidine units to one or more small molecules/small molecule fragments/functional groups to form guanylurea units with the small molecules/small molecule fragments/modifications.

In one embodiment, the subject invention provides a method of preparing a peptide-active agent of the subject invention. The method comprises providing a tritylated peptide, poly(amino acid)s or protein comprising a guanylurea linked to a small molecule/small molecule fragment/modification; and coupling the tritylated peptide, poly(amino acid)s or protein to a drug through a linker to form a peptide-active agent.

In one embodiment, the subject invention provides a method of preparing a CPP-NP of the subject invention, comprising: providing a tritylated peptide comprising a guanylurea linked to a small molecule; coupling the tritylated peptide to a drug through a linker to provide a drug comprising peptide; and combining the drug comprising peptide with a crosslinker to form a CPP-NP. In a specific embodiment, the crosslinker is a bis-boronic acid.

In one embodiment, the subject invention further provides methods for treating a cancer/tumor, the method comprising administering, to a subject in need of such treatment, an effective amount of the therapeutic formulation/composition of the subject invention.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being. Treating can also include preventing a condition or disorder, which, as used herein, means delaying the onset of, or progression of, a particular sign or symptom of the condition or disorder.

The compositions can be administered to a subject by methods including, but not limited to, (i) administration through oral pathways, which administration includes administration in capsule, tablet, granule, spray, syrup, or other such forms; (ii) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (iii) administration topically, or as deemed appropriate by those of skill in the art for bringing the compound into contact with living tissue; and (iv) administration via controlled released formulations, depot formulations, and infusion pump delivery.

In certain embodiments, the peptide-active agent/CPP and/or ADC of the subject invention provides treatment for cancers including, but not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer including, for example, HER2-positive breast cancer, colon cancer, rectal myeloma and B-cell lymphoma, brain cancer, head and neck cancers, and associated metastases.

The peptide-active agent/CPP and/or ADC of the subject invention can also be used to deliver active agents for the treatment of a variety of other conditions including, but not limited to, inflammatory disorders, autoimmune disorders, disorders of the nervous system, and cardiovascular disorders.

In one embodiment, the subject invention provides methods for targeted delivery of a compound or molecule, such as therapeutic agents (e.g., drugs, antibodies, DNAs, RNAs such as siRNAs and miRNAs, peptides and proteins), into cells, preferably, cancer cells, the method comprising contacting the cells with the linker molecule, peptide-active agent/CPP/ADC or the therapeutic formulation/composition of the subject invention.

In one embodiment, the subject invention provides methods for targeted delivery of a therapeutic agent into cells, preferably, cancer cells, the method comprising contacting the cells with the linker molecules of the subject invention and the therapeutic agent.

In one embodiment, the subject invention provides methods for transporting a compound or molecule, including therapeutic agents (e.g., drugs, dye molecules, antibodies, DNAs, RNAs such as siRNAs and miRNAs, peptides and proteins), across a biological membrane, the method comprising contacting the biological membrane with the linker molecule, peptide-active agent/CPP and/or ADC or the therapeutic formulation/composition of the subject invention. The biological membrane may be, for example, cell membranes, organelle membranes, mucous membranes, basement membranes, and serous membranes.

In one embodiment, the subject invention provides methods for transporting a therapeutic agent across a biological membrane, the method comprising contacting the biological membrane with the linker molecule of the subject invention and the therapeutic agent.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

As used herein, each of m, n, o, p, x, y and z is intended to include ≥0, ≥1, ≥2, ≥3, ≥4, ≥5, ≥6, ≥7, ≥8, ≥9, ≥10, ≥11, ≥12, ≥13, ≥14, ≥15, ≥16, ≥17, ≥18, ≥19, ≥20, ≥21, ≥22, ≥23, ≥24, ≥25, ≥26, ≥27, ≥28, ≥29, ≥30, ≥31, ≥32, ≥33, ≥34, ≥35, ≥36, 237, 38, ≥39, ≥40, ≥41, ≥42, ≥43, ≥44, ≥45, ≥46, ≥47, ≥48, ≥49, ≥50, ≥51, ≥52, ≥53, ≥54, ≥55, ≥56, ≥57, ≥58, ≥59, ≥60, ≥61, ≥62, ≥63, ≥64, ≥65, ≥66, ≥67, ≥68, ≥69, ≥70, ≥71, ≥72, ≥73, ≥74, ≥75, ≥76, ≥77, ≥78, ≥79, ≥80, ≥81, ≥82, ≥83, ≥84, ≥85, ≥86, ≥87, ≥88, ≥89, ≥90, ≥91, ≥92, ≥93, ≥94, ≥95, ≥96, ≥97, ≥98, ≥99, and ≥100.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

EXAMPLES

Example 1—Synthesis of cisPt-R8-G

Figure 5:
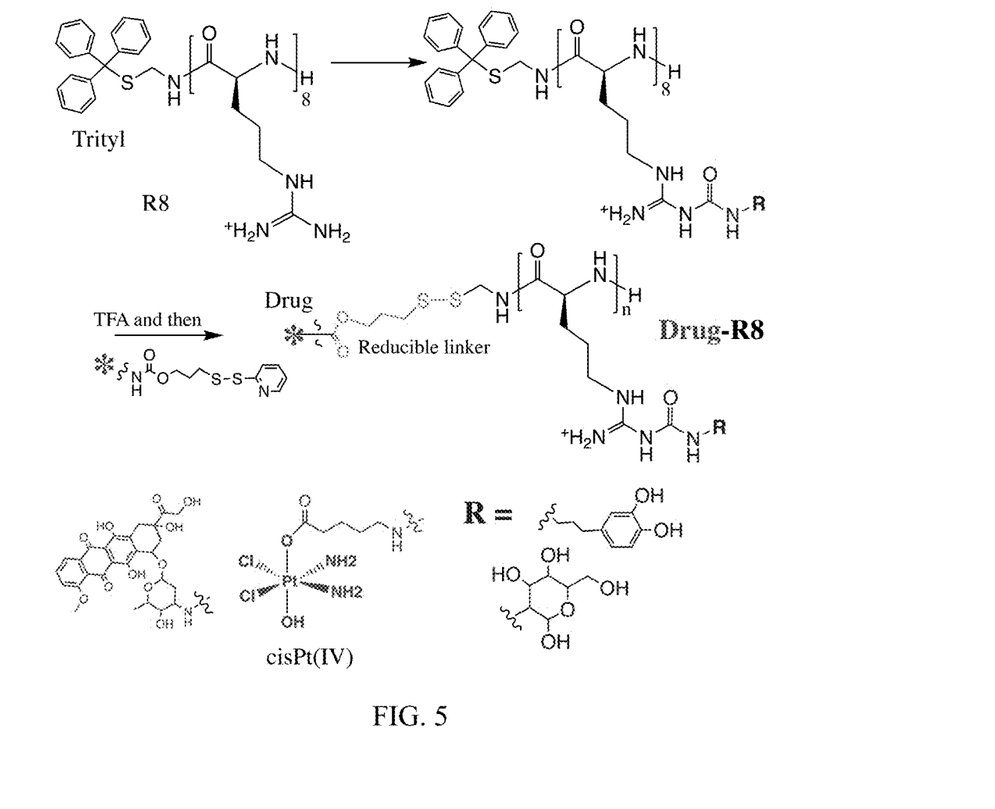
FIG. 5 shows a reaction scheme for the formation of a CPP by formation of a guanylurea attachment of a polyol at every amino acid repeating unit and an end-functionalized drug, according to an embodiment of the invention, from a tritylsulfide.

Commercially available tritylated R8 reacts with isocyanate-converted glucosamine as indicated in FIG. 5. The primary amine group of O-acetylated glucosamine is converted to an isocyanate using triphosgene. Synthesis and purification of cisPt-R8-G is conducted using modified literature procedures.

Synthesis of cisPt (IV) Prodrug and Conjugation to R8-G

The analogue of a platinum (II) anti-cancer drug, for example, Cisplatin, a platinum (IV) pro-drug [cisPt (IV)] has been synthesized. These pro-drugs overcome drug resistance and can be coupled by various functional units to targeted delivery systems. Two coordination sites at the axial position of Pt (IV) are modified for coupling to peptides, polymers, or nanoparticles. An axial position of Pt (IV) is further modified with a reducible disulfide linker to couple to the thiolate R8-G, as shown in FIG. 5. The other axial position remains available for further modification with either hydrophobic or certain intracellular organelle targeting groups, as desired. The Pt (II) compound is oxidized using $H_2O_2$ to Pt (IV) having hydroxyl groups at the axial position. The hydroxyl groups react with a primary amine-containing linker to add a 2-pyridylthio functional group. Upon reaction with thiolate R8-G, the cisPt is coupled to the peptide by a reducible disulfide linker. Variation in the linker length allows manipulation of the intracellular degradation kinetics for the modulation of the drug release kinetics. A similar synthetic and purification technique can be applied to the synthesis of Dox-R8-G.

Peptide NPs Formation

Figure 6:
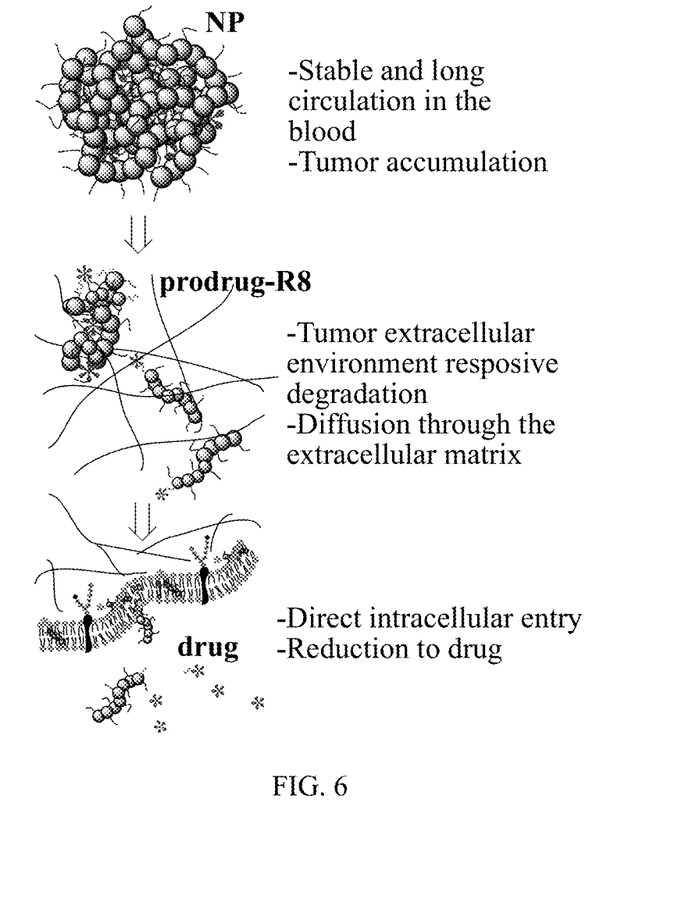
FIG. 6 shows a CPP-comprising NP, according to an embodiment of the invention, and the acid catalyzed degradation of the NP to a prodrug-coupled CPP and the intracellular reduction of the disulfide linker for the drug to release the drug in the tumor cell.
Figure 7:
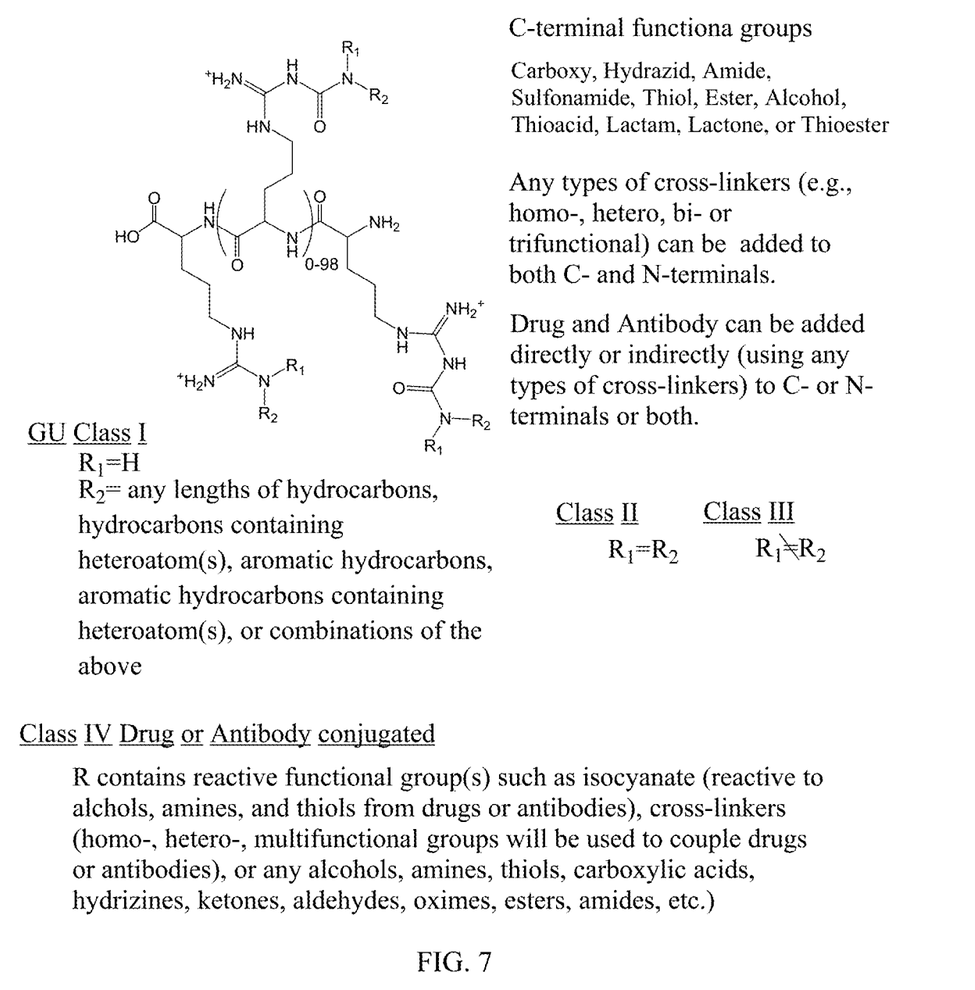
FIG. 7 shows a peptide scheme of the linker molecule.

Boronic acids form stable ester bonds with the hydroxyl groups of sugar units at neutral or basic conditions where the boronic ester bonds are degraded at the acidic pH. Crosslinkers, as shown in FIG. 5 are synthesized by reacting adipic acid and 2-aminophenylboronic acid by a standard carbodiimide coupling reaction. The Pt(IV)-containing phenylboronic acid is synthesized by a literature procedure. The crosslinker results in highly crosslinked NPs, as illustrated in FIG. 6, while maintaining a high Pt concentration. By controlling the mole ratios between the peptide and the crosslinker(s), sugar-coated charge-modulated peptide NPs of 50-100 nm are formed.

NP Degradation

Using the dialysis techniques (i.e., 3.5K or 10K molecular weight cut-off membrane tube or cassette), the degradation of peptide NPs under acidic conditions (pH 6.5-6.8 for extracellular matrix and 7.4 for blood circulation) reflect the stability/degradation kinetics. Because the extracellular glutathione concentration, 2-20 μM, is much lower than intracellular concentration, 2-10 mM, and due to inaccessible disulfide bonds between the drug and peptide, the reducible linker of FIG. 3 and FIG. 5, because of the crosslinking, display no premature Pt release by reduction. The NP maintains its integrity during circulation, but, as shown in FIG. 6, undergoes fast degradation to drug-R8-G at the tumor extracellular environments.

Example 2—Synthesis of Drug-Conjugated Octaarginine-Based Linkers

Synthesis of Dox-Y-R8-SMPB and Dox-Y-R8(GU-PD)-SMPB

Figure 8:
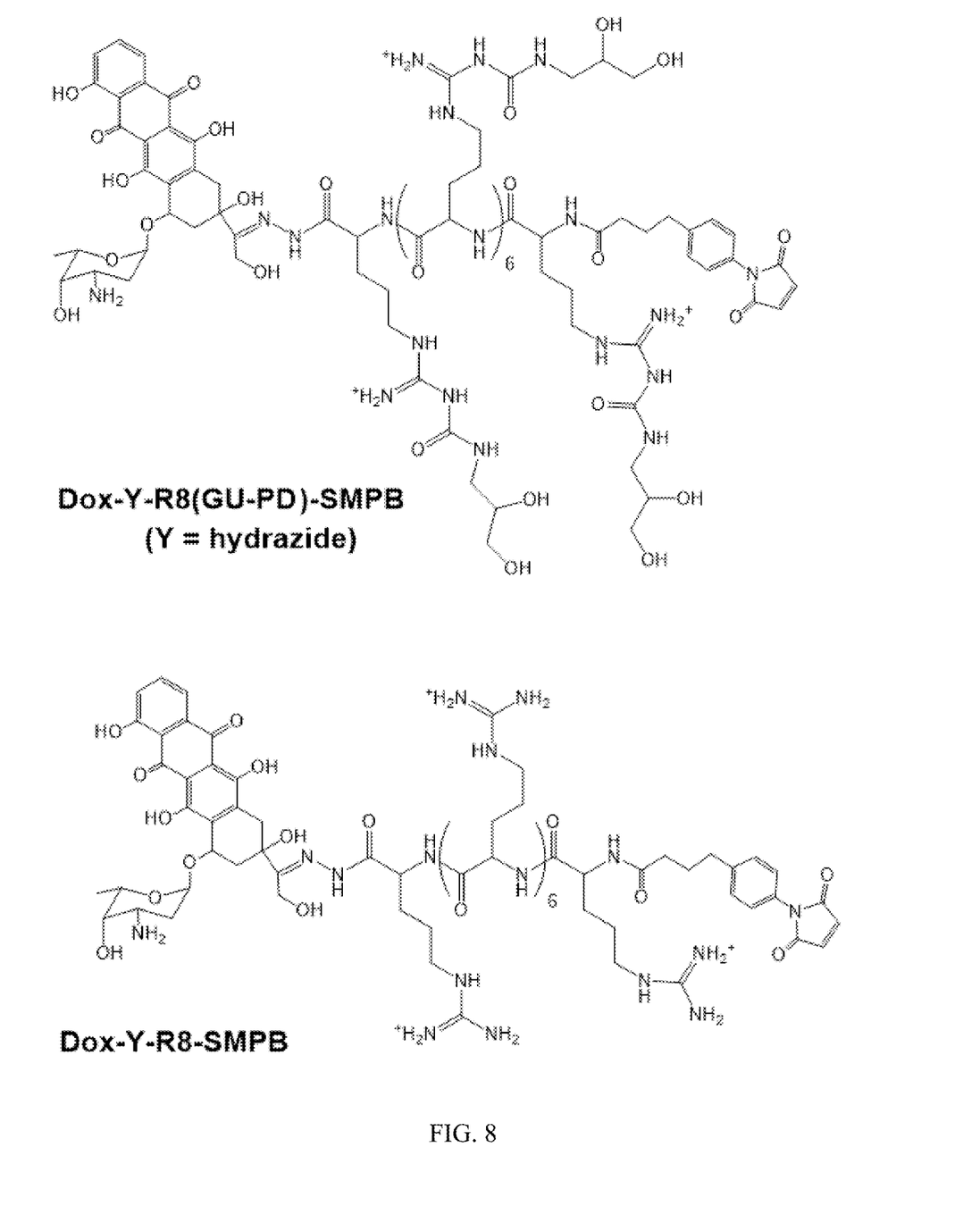
FIG. 8 shows the structures of Dox-Y-R8(GU-PD)-SMPB and Dox-Y-R8-SMPB.

Dox-Y-R8(GU-PD)-SMPB is synthesized as the target linker for antibody coupling. Dox-Y-R8-SMPB is the control. The solid phase synthetic technique is used to synthesize these structures. Preparatory HPLC is used to purify the drug-coupled peptide linkers. Various spectroscopic techniques including UV, NMR, FTIR, and Mass spectroscopy are used to characterize the linkers As shown in FIG. 8, the N-terminus of R8 can be reacted with succinimidyl 4-(p-maleimidophenyl)butyrate (SMPB) to have the maleimide functional group. Her2 is covalently attached to the linker through the thiol-ene reaction at the maleimide group. The C-terminal of R8 is coupled to doxorubicin (Dox) to using a hydrazide functional group. Instead of coupling a fluorophore, the coupling of Dox will have advantages even at this phase because Dox has the intrinsic fluorescent property that can be tracked for the cellular entry, localization, and release behaviors. Also, by comparing cytotoxicity among the linkers as well as free Dox, the toxicity of the linkers is evaluated. The coupling chemistry of Dox is the hydrazone formation reaction by reacting the hydrazide of R8 and the ketone group of Dox. This acid labile group helps the intracellular release of Dox. A more stable amide bond between R8 and Dox may be used for enhanced stability.

The choice of functional group in the arginine side chain is propanediol (PD). Compared to glucosamine (shown in FIG. 2), PD has better positive charge screening effects, while synthesis/purification of guanylurea functionalized R8 can be more feasible compared to glucosamine. PD has two alcohols that will interact with the membrane phosphate groups via hydrogen bonding. PD modulated R8 shows better or similar cellular entry comparable to non-modified R8 control.

Evaluation of In Vitro Properties of the Linkers.

The hydrazone hydrolysis behaviors is conducted by incubating the linker in acidic to neutral buffers (e.g., pH 4.5-7.4). Fluorescent confocal microscopy and flow cytometry are used to evaluate the cellular entry kinetics and mechanism of the linkers. Various fluorescent assays are conducted to assess cell viability, apoptosis, and cell death. ATP consumption in live cells is monitored using a luminescent assay kit (i.e., CellTiter-Glo for cell viability assay).

In Vitro and In Vivo Evaluation of the Dox-R8-Anti-Her and Dox-R8(GU-PD)-Anti-Her An in vivo study is conducted to evaluate blood circulation time of the guanylurea-modified R8 compared with conventional positively charged R8. The model ADC (Dox-R8(GUPD)-anti-Her) is evaluated in vivo in ICR mice for their pharmacokinetics and biodistribution (i.e., plasma half-life, clearance, distribution volumes and organ uptake) and compared against control (Dox-R8-anti-Her). Pharmacokinetics parameters are estimated using a 2-compartment model with bolus injection and central compartment elimination. The ADCs, developed according the subject invention, are administered by tail vein injection. At 6, 12, 24, 48, or 72 hours after administration, the animals are euthanized by an overdose of isoflurane. Following euthanasia, approximately 1 g of blood, lung, liver, kidney, heart, skeletal muscle, and spleen are collected and imaged for relative fluorescence analysis. Also, Dox may be replaced by a dye molecule.

The maximum tolerance dose (MTD) is determined by an intravenous injection of various single doses of ADCs, and the weight and physical states of the mice are monitored for 10 d. The MTD is the highest dose at which weight loss is <20% and recovers. The clinical chemistry parameters (i.e., the blood urea nitrogen and creatine levels) indicate renal toxicity. An increased level of aspartate aminotransferase indicates possible hepatoxicity.

Evaluation of In Vitro Properties of the Linkers

The linkers exhibit no severe cell toxicity. Indeed, the guanylurea chemistry lowers the intrinsic toxicity originated from the positive charge of many carriers. In order to evaluate any potential cellular toxicity of the linker, cytotoxicity and cellular entry pathways of the linker are evaluated using Hela cells. Fluorescent confocal microscopy and flow cytometry are used to evaluate the cellular entry kinetics and mechanism. Various fluorescent assays are conducted to assess cell viability, apoptosis, and cell death. ATP consumption in live cells is monitored using a luminescent as-say kit (i.e., CellTiter-Glo for cell viability assay).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A peptide comprising an oligopeptide or polypeptide, a plurality of the amino acid residues of the oligopeptide or polypeptide comprising a positively charged guanylurea unit with a small molecule fragment or modification, the small molecule fragment being a polyol comprising 2 to 20 hydroxy groups.

2. The peptide according to claim 1, the polyol being a sugar.

3. The peptide according to claim 1, which is further end-functionalized by an active agent, wherein the active agent is attached to the peptide through a linker.

4. The peptide according to claim 3, wherein the linker is selected from the group consisting of a hydrazone, azide, oxyme, maleimide, ester, amide, and a disulfide.

5. The peptide according to claim 3, wherein the active agent is a drug or detectable entity.

6. The peptide according to claim 5, wherein the drug is selected from the group consisting of a radio therapeutic, doxorubicin, paclitaxel, thapsigargin, cyclosporine A, and cis-platin.

7. The peptide according to claim 1, the oligopeptide or polypeptide further comprising amino acids having the positively charged guanylurea unit functionalized with a cross-linker.

8. The peptide of claim 3, which is further end-functionalized with a targeting moiety, wherein the end of the peptide that is functionalized with the targeting moiety is a different end of the peptide as compared with the end of the peptide that is functionalized with the active agent.

9. The peptide of claim 8, wherein the targeting moiety is an antibody.

10. The peptide of claim 1, wherein the amino acids in the oligopeptide or polypeptide that comprise a positively charged guanylurea unit with a small molecule fragment or modification, the small molecule fragment being a polyol comprising 2 to 20 hydroxy groups are arginine amino acids.

11. The peptide of claim 10, wherein the oligopeptide or polypeptide comprises 1 to about 500 arginine amino acids.

12. The peptide of claim 11, wherein the oligopeptide comprises 1 to 30 arginine amino acids.

13. The peptide of claim 1, wherein the small molecule fragment being a polyol comprising 2 to 20 hydroxy groups is 14. The peptide of claim 3, which has been further combined with bis-boronic acid.

15. A method for treating a cancer comprising administering, to a subject in need of such treatment, the peptide according to claim 6, wherein the drug is selected from the group consisting of a radio therapeutic, doxorubicin, paclitaxel, thapsigargin, cyclosporine A, and cis-platin.

16. A method for delivering a therapeutic agent into a cancer cell, comprising contacting the cancer cell with the peptide according to claim 6.

\* \* \* \* \*